United States Patent
Feng et al.

(10) Patent No.: US 10,815,208 B2
(45) Date of Patent: Oct. 27, 2020

(54) METHOD FOR PREPARING 2-HYDROXYL-4-(2, 3-DISUBSTITUTED BENZYLOXY)-5-SUBSTITUTED BENZALDEHYDE DERIVATIVE

(71) Applicants: Institute of Materia Medica, Chinese Academy of Medical Sciences, Beijing (CN); Tianjin Chase Sun Pharmaceutical Co., LTD, Tianjin (CN)

(72) Inventors: Zhiqiang Feng, Beijing (CN); Xiaoguang Chen, Beijing (CN); Yang Yang, Beijing (CN); Fangfang Lai, Beijing (CN)

(73) Assignees: Institute of Materia Medica, Chinese Academy of Medical Sciences, Beijing (CN); Tianjin Chase Sun Pharmaceutical Co., LTD, Tianjin (CN)

( * ) Notice: Subject to any disclaimer, the term of this patent is extended or adjusted under 35 U.S.C. 154(b) by 0 days.

(21) Appl. No.: 16/303,650

(22) PCT Filed: May 23, 2017

(86) PCT No.: PCT/CN2017/085421
§ 371 (c)(1),
(2) Date: Nov. 15, 2019

(87) PCT Pub. No.: WO2017/202277
PCT Pub. Date: Nov. 30, 2017

(65) Prior Publication Data
US 2020/0181115 A1    Jun. 11, 2020

(30) Foreign Application Priority Data

May 23, 2016  (CN) .......................... 2016 1 0343960

(51) Int. Cl.
| | | |
|---|---|---|
| *C07D 401/14* | (2006.01) | |
| *C07D 295/155* | (2006.01) | |
| *C07C 233/36* | (2006.01) | |
| *C07C 255/54* | (2006.01) | |
| *C07D 405/12* | (2006.01) | |

(Continued)

(52) U.S. Cl.
CPC .......... *C07D 295/155* (2013.01); *A61P 35/00* (2018.01); *C07C 45/61* (2013.01); *C07C 211/29* (2013.01); *C07C 227/12* (2013.01); *C07C 229/36* (2013.01); *C07C 231/12* (2013.01); *C07C 233/36* (2013.01); *C07C 235/34* (2013.01); *C07C 255/54* (2013.01); *C07C 269/02* (2013.01); *C07C 271/64* (2013.01); *C07C 311/05* (2013.01); *C07D 207/08* (2013.01); *C07D 207/16* (2013.01); *C07D 221/00* (2013.01); *C07D 265/30* (2013.01); *C07D 309/14* (2013.01); *C07D 319/16* (2013.01); *C07D 319/18* (2013.01); *C07D 401/14* (2013.01); *C07D 405/12* (2013.01); *C07D 407/12* (2013.01);

(Continued)

(58) Field of Classification Search
CPC .. C07D 407/12; C07D 319/18; C07D 211/60; C07D 405/12; C07D 309/14; C07D 207/08; C07D 265/30; C07D 401/12; C07C 17/263; C07C 255/54; C07C 17/14; C07C 25/18
USPC ....................................................... 546/256
See application file for complete search history.

(56) References Cited

U.S. PATENT DOCUMENTS

| 4,329,518 A | 5/1982 | Plummer et al. |
| 2015/0291549 A1 | 10/2015 | Chupak et al. |

(Continued)

FOREIGN PATENT DOCUMENTS

| CN | 1735408 | 2/2006 |
| CN | 103787902 A | 5/2014 |

(Continued)

OTHER PUBLICATIONS

International Search Repot and Written Opinion for PCT/CN2017/085420, dated Aug. 9, 2018.

(Continued)

Primary Examiner — Taylor V Oh
(74) *Attorney, Agent, or Firm* — Wolf, Greenfield & Sacks, P.C.

(57) ABSTRACT

Provided is a method for preparing 2-hydroxy-4-(2, 3-disubstituted benzyloxy)-5-substituted benzaldehyde derivative represented by formula (I). The method comprises the following steps: (1) preparing 3-aryl-2-substituted toluene derivative 2 by using 3-iodo-2-substituted toluene derivative 1 and aryl boronic acid 5 or aryl boronate as starting materials; (2) preparing a benzyl halide derivative 3 by using 3-aryl-2-substituted toluene derivative 2 as starting materials; and (3) preparing 4-(2, 3-disubstituted benzyloxy)-2-hydroxy-5-substituted benzaldehyde derivative (I) by using benzyl halide derivative 3 and 2,4-dihydroxy-5-substituted benzaldehyde 6.

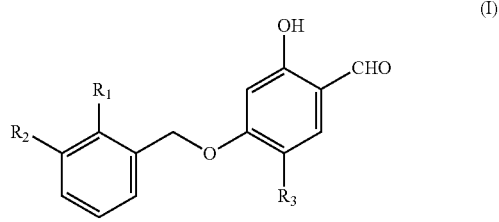

10 Claims, No Drawings

(51) Int. Cl.
| | |
|---|---|
| C07C 311/05 | (2006.01) |
| C07D 319/18 | (2006.01) |
| C07D 207/16 | (2006.01) |
| C07C 45/61 | (2006.01) |
| C07C 231/12 | (2006.01) |
| A61P 35/00 | (2006.01) |
| C07C 211/29 | (2006.01) |
| C07C 229/36 | (2006.01) |
| C07C 235/34 | (2006.01) |
| C07D 221/00 | (2006.01) |
| C07D 265/30 | (2006.01) |
| C07D 407/12 | (2006.01) |
| C07C 227/12 | (2006.01) |
| C07C 269/02 | (2006.01) |
| C07C 271/64 | (2006.01) |
| C07D 207/08 | (2006.01) |
| C07D 309/14 | (2006.01) |
| C07D 319/16 | (2006.01) |
| A61K 31/36 | (2006.01) |
| A61K 31/165 | (2006.01) |
| A61K 31/277 | (2006.01) |
| A61K 45/06 | (2006.01) |

(52) U.S. Cl.
CPC .......... *A61K 31/165* (2013.01); *A61K 31/277* (2013.01); *A61K 31/36* (2013.01); *A61K 45/06* (2013.01)

(56) References Cited

U.S. PATENT DOCUMENTS

| | | |
|---|---|---|
| 2019/0233405 A1 | 8/2019 | Feng et al. |
| 2019/0241531 A1 | 8/2019 | Feng et al. |
| 2020/0055819 A1 | 2/2020 | Feng et al. |

FOREIGN PATENT DOCUMENTS

| | | |
|---|---|---|
| WO | WO 2007/106469 | 9/2007 |
| WO | WO 2013/126428 | 8/2013 |
| WO | WO 2015/034820 A1 | 3/2015 |
| WO | WO 2015/160641 A2 | 10/2015 |

OTHER PUBLICATIONS

International Preliminary Report on Patentability for PCT/CN2017/085420, dated Nov. 27, 2018.
International Search Repot and Written Opinion for PCT/CN2017/085417, dated Aug. 2, 2017.
International Preliminary Report on Patentability for PCT/CN2017/085417, dated Nov. 27, 2018.
International Search Repot and Written Opinion for PCT/CN2017/085418, dated Aug. 9, 2017.
International Preliminary Report on Patentability for PCT/CN2017/085418, dated Nov. 27, 2018.
International Search Repot and Written Opinion for PCT/CN2017/085421, dated Aug. 9, 2017.
International Preliminary Report on Patentability for PCT/CN2017/085421, dated Nov. 27, 2018.
Kusuma et al., Synthesis and Evaluation of Novologues as C-Terminal Hsp90 Inhibitors with Cytoprotective Activity against Sensory Neuron Glucotoxicity. J. Med. Chem., 2012;55(12):5797-5812. DOI: 10.1021/jm300544c.
Sasaki et al., Design, synthesis, and biological activity of potent and orally available G protein-coupled receptor 40 agonists. J Med Chem. Mar. 10, 2011;54(5):1365-78. doi: 10.1021/jm101405t. Epub Feb. 14, 2011.
Smith et al., Suzuki and Heck Coupling Reactions Mediated by Palladium Complexes Bearing trans-Spanning Diphosphines. Journal of Organometallic Chemistry Jan. 2005;690(2):477-481.
Yao et al., An efficient multistep ligand-based virtual screening approach for GPR40 agonists. Molecular Diversity Dec. 5, 2013;18(1):183-193.
*U.S. Appl. No. 16/303,641, filed Nov. 20, 2018, Feng et al.
*U.S. Appl. No. 16/303,646 filed Nov. 20, 2018, Feng et al.
*U.S. Appl. No. 16/303,649, filed Nov. 20, 2018, Feng et al.
Extended European Search Report for Application No. Ep 17802122.6 dated Feb. 12, 2020.
Extended European Search Report for Application No. EP 17802123.4 dated Feb. 12, 2020.
[No Author Listed] Expert Scientific Group on Phase One Clinical Trials Final Report. Nov. 30, 2006. pp. C1, C35-C38.
DAS, Current and emerging strategies for the treatment and management of systemic lupus erythematosus based on molecular signatures of acute and chronic inflammation. J Inflamm Res. 2010;3:143-170. doi:10.2147/JIR.S9425.
Hartung et al., What do we know about the mechanism of action of disease-modifying treatments in MS?. J Neurol. 2004;251 Suppl 5:v12-v29. doi:10.1007/s00415-004-1504-y.
McMahon, VEGF receptor signaling in tumor angiogenesis. Oncologist. 2000;5 Suppl 1:3-10. doi:10.1634/theoncologist.5-suppl_1-3.
Neidle, Cancer Drug Design and Discovery. Elsevier. 2008:427-431.
Pinedo et al., Translational Research: the Role of VEGF in Tumor Angiogenesis. Oncologist. 2000;5 Suppl 1:1-2.
Tanc et al., 7-Substituted-sulfocoumarins are isoform-selective, potent carbonic anhydrase II inhibitors. Bioorg Med Chem. 2013;21(15):4502-4510. doi:10.1016/j.bmc.2013.05.032.
Wang et al., Anti-inflammatory properties and regulatory mechanism of a novel derivative of artemisinin in experimental autoimmune encephalomyelitis. J Immunol. 2007;179(9):5958-5965. doi:10.4049/jimmunol.179.9.5958.
EP 17802122.6, Feb. 12, 2020, Extended European Search Report.
EP 17802123.4, Feb. 12, 2020, Extended European Search Report.

METHOD FOR PREPARING 2-HYDROXYL-4-(2, 3-DISUBSTITUTED BENZYLOXY)-5-SUBSTITUTED BENZALDEHYDE DERIVATIVE

RELATED APPLICATIONS

This application is a national stage filing under 35 U.S.C. § 371 of international PCT application, PCT/CN2017/085421, filed May 23, 2017, which claims priority to Chinese Application No. 201610343960.7, filed on May 23, 2016.

TECHNICAL FIELD

The invention relates to a preparation method of a compound of the formula (I), that is, a 4-(2,3-disubstituted benzyloxy)-2-hydroxy-5-substituted benzaldehyde derivative, and belongs to the technical field of medicine.

BACKGROUND TECHNOLOGY

With the deepening of research on cancer immunology, it has been found that the tumor microenvironment can protect tumor cells from being recognized and killed by the human immune system. The immune escape of tumor cells plays a very important role in tumor occurrence and development. In 2013, Science magazine ranked tumor immunotherapy as the first of the top ten breakthroughs, once again making immunotherapy a "focus" in the field of cancer treatment. Activation or inhibition of immune cells is regulated by positive and negative signals, wherein programmed cell death 1 (PD-1)/PD-1 ligand (PD-L1) is a negative immune regulatory signal that inhibits the immune activity of tumor-specific CD8+ T cells and mediates immune escape.

Tumor cells evade the immune system by the binding of programmed cell death ligand (PD-L1) produced on its surface to the PD-1 protein of T cells. The tumor microenvironment induces high expression of PD-1 molecules in infiltrating T cells, and tumor cells highly express PD-1 ligands PD-L1 and PD-L2, resulting in continuous activation of the PD-1 pathway in the tumor microenviroment. The inhibited T cells cannot find the tumor so that it cannot signal the immune system to attack and kill the tumor cells. The PD-1 antibody against PD-1 or PD-L1 blocks this pathway by preventing the two proteins from binding and partially restores the function of T cells, enabling them to kill tumor cells.

PD-1/PD-L1-based immunotherapy is a new generation high-profile immunotherapy, aiming to use the body's own immune system to fight tumors. It has the potential to treat multiple types of tumors by blocking the PD-1/PD-L1 signaling pathway to induce apoptosis. Recently, a series of surprising studies have confirmed that PD-1/PD-L1 inhibitory antibodies have strong anti-tumor activity against a variety of tumors, which is particularly eye-catching. On Sep. 4, 2014, Keytruda® (pembrolizumab) from Merck, USA, became the first FDA-approved PD-1 monoclonal antibody for the treatment of advanced or unresectable melanoma patients who were unresponsive for other medications. Currently, MSD is investigating the potential of Keytruda in more than 30 different types of cancer, including various types of blood cancer, lung cancer, breast cancer, bladder cancer, stomach cancer, and head and neck cancer. On Dec. 22, 2014, pharmaceutical giant Bristol-Myers Squibb took the lead in obtaining accelerated approval from the US Food and Drug Administration (FDA). Its anti-cancer immunotherapy drug nivolumab was listed under the trade name Opdivo for the treatment of unresectable or metastatic melanoma patients who have not responded to other drugs and it is the second US-listed PD-1 inhibitor after MSD's Keytruda. On Mar. 4, 2015, FDA approved nivolumab for the treatment of metastatic squamous non-small cell lung cancer that progressed during platinum-based chemotherapy or after chemotherapy. According to a Phase Ib KEYNOTE-028 study of the treatment of solid tumors by Keytruda (pembrolizumab) published by MSD, Keytruda treatment achieved a 28% overall response rate (ORR) in 25 patients with pleural mesothelioma (PM). And 48% of patients have stable disease and the disease control rate has reached 76%. Patients with advanced Hodgkin's lymphoma (HL) who had no treatment response to any of the approved drugs were able to achieve complete remission after receiving treatment with MSD's Keytruda and Bristol-Myers' Opdvio. At the 2015 AACR Annual Meeting, Leisha A. Emens, MD, PhD, associate professor of oncology at the Johns Hopkins Kimmel Cancer Center, reported that Roche's PD-L1 monoclonal antibody MPDL3280A has a long-lasting effect in advanced triple-negative breast cancer.

Tumor immunotherapy is considered a revolution in cancer treatment after tumor targeting therapy. However, the monoclonal antibody therapeutic drug has its own defects: it is easily decomposed by proteases, so it is unstable within the body and cannot be taken orally; it is easy to produce immune cross-reaction; the product quality is not easy to control and the production technology is high; a large amount of preparation and purification is difficult, and the cost is high; it is inconvenient to use and it only can be injected or drip. Therefore, small molecule inhibitors of PD-1/PD-L1 interaction are a better choice for tumor immunotherapy.

The 4-(2,3-disubstituted benzyloxy)-2-hydroxy-5-substituted benzaldehyde derivative represented by the formula (I) of the present invention is an important intermediate of an immunomodulator acting on PD1/PD-L1 and such immunomodulator is mainly used for cancer, infectious diseases and autoimmune diseases.

At present, the methods for the preparation of a part of 4-(2,3-disubstituted benzyloxy)-2-hydroxy-5-substituted benzaldehyde derivative (I) are not sufficiently high in yield and not suitable for industrial production.

SUMMARY OF THE INVENTION

The technical problem to be solved by the present invention is to provide a method for preparing 4-(2,3-disubstituted benzyloxy)-2-hydroxy-5-substituted benzaldehyde derivative (I) as a potential pharmaceutical intermediate.

For the purpose of the present invention, 4-(2,3-disubstituted benzyloxy)-2-hydroxy-5-substituted benzaldehyde derivative (I) is prepared by the following technical scheme.

The technical scheme includes the following steps:

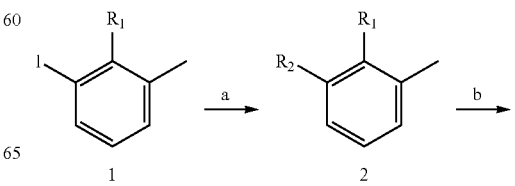

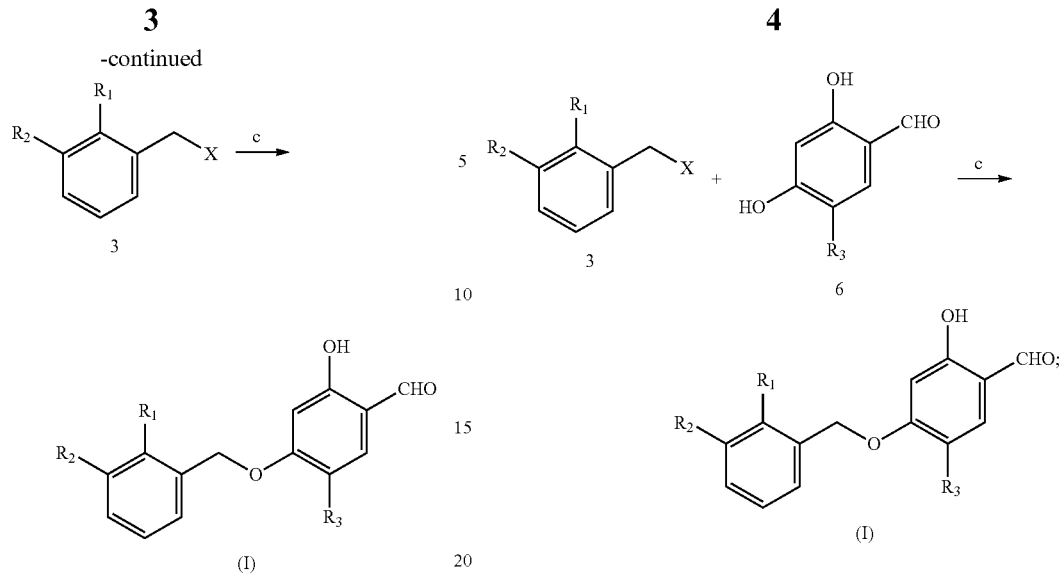

wherein: R1=fluorine, chlorine, bromine, methyl, cyano;

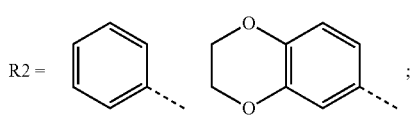

R3=hydrogen, methyl, ethyl, fluorine, chlorine, bromine; and

X is selected from bromine, chlorine, and iodine.

The preferred scheme includes the following steps:

(1) preparing 3-aryl-2-substituted toluene derivative 2 from 2-substituted-3-iodotoluene derivative 1 and aryl boronic acid 5 or aryl boronate as starting materials;

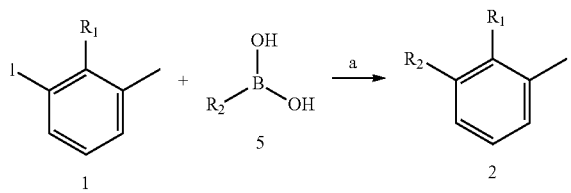

(2) preparing benzyl halide derivative 3 from 2-substituted-3-aryltoluene derivative 2 as a starting material;

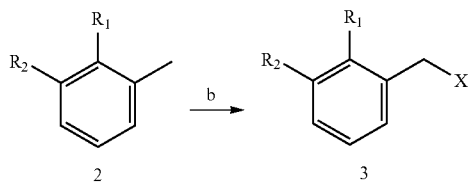

(3) preparing 4-(2,3-disubstituted benzyloxy)-2-hydroxy-5-substituted benzaldehyde derivative (I) from benzyl halide derivative 3 and 2,4-dihydroxy-5-substituted benzaldehyde 6 as starting materials;

R1=fluorine, chlorine, bromine, methyl, cyano;

R2 = [phenyl, benzodioxine];

R3=hydrogen, methyl, ethyl, fluorine, chlorine, bromine;
X is selected from bromine, chlorine, and iodine.

The solvents can be dried in a conventional manner in the field for use.

Specifically, the preparation method of the present invention is as follows:

Step (1): Preparation of 2-substituted-3-aryltoluene Derivative 2

The starting materials of step (1) are 2-substituted-3-iodotoluene derivative 1 and aryl boronic acid 5 or aryl boronate in a molar ratio of 1:0.8-1.5; preferably 1:1.

The reaction is carried out in a conventional chemical reaction vessel, such as a flask or a reactor. Preferably, the reaction vessel is dried.

The solvent used for the reaction may be a protic solvent, an aprotic solvent, a polar solvent, a non-polar solvent, or a mixed solvent for the purpose of dissolving the reactants. Preferred aprotic solvents are selected from tetrahydrofuran, diethyl ether, dioxane, dimethyl sulfoxide, toluene, N,N-dimethylformamide; preferred protic solvents are selected from ethanol, isopropanol, methanol, tert-butanol, water, formic acid, acetic acid, ethylamine; the most preferred solvent is selected from dioxane/water, preferably in a volume ratio of from 1 to 10:1, most preferably 5:1.

Preferred palladium catalyst for the reaction is zero-valent palladium or divalent palladium compound; more preferred is triphenylphosphine palladium, or tetrakis(triphenyl phosphine)palladium, or $PdCl_2(dppf)$; and the most preferred is tetrakis(triphenylphosphine)palladium.

The preferred base for the reaction may be selected from alkali metal carbonate, alkali metal acetate, alkali metal hydroxide and alkaline earth metal hydroxide, alkali metal fluoride, alkali metal phosphate; more preferred is cesium carbonate, potassium carbonate, sodium carbonate, sodium acetate, potassium acetate, cesium acetate, cesium hydroxide, potassium hydroxide, sodium hydroxide, barium hydroxide, potassium fluoride, cesium fluoride, potassium phosphate, cesium phosphate, sodium phosphate; the most preferred is cesium carbonate, cesium acetate, barium hydroxide, cesium phosphate.

The reaction condition is preferably under the protection of an inert gas, most preferably argon gas; the reaction condition is preferably to control the reaction temperature, and the reaction temperature can be controlled between the room temperature and 120° C., and preferably 100° C. The reaction temperature varies depending on the solvent.

Step (2): Preparation of Benzyl Halide Derivative 3

In step (2), 2-substituted-3-aryltoluene derivative 2 is used as a starting material for the preparation of benzyl halide derivative 3.

In the step (2), 2-substituted-3-aryltoluene derivative 2 is reacted with a brominating agent under a free radical initiating condition for the preparation of benzyl halide derivative 3. A molar ratio of 2-substituted-3-aryltoluene derivative 2 to brominating agent is 1:0.8-1.5; most preferably 1:1; and a molar ratio of the brominating agent to the free radical initiator is 1:0.01-0.10; most preferably 1:0.05.

Preferred brominating agent for the reaction may be NCS (N-chlorosuccinimide), NBS (N-bromosuccinimide), TBAB (phenyltrimethylammonium tribromide), elemental bromine; the most preferred brominating agent is NBS.

Preferred free radical initiating condition for the reaction is the addition of a free radical initiator, light, or both; more preferably the addition of a free radical initiator; particularly preferred is benzoyl peroxide, m-chloroperoxybenzoic acid; the most preferred is benzoyl peroxide.

The reaction is carried out in a conventional chemical reaction vessel or in an actinic reactor, such as a flask or a tailored actinic reactor. Preferably, the reaction vessel is dried.

The solvent used in the reaction is preferably selected from carbon tetrachloride, carbon tetrabromide, acetonitrile; most preferably carbon tetrachloride.

The reaction condition is preferably to control the reaction temperature, and the reaction temperature can be controlled between 50 and 85° C., and preferably 80° C. The reaction temperature varies depending on the solvent.

Step (3): Preparation of 4-(2,3-Disubstituted benzyloxy)-2-hydroxy-5-substituted Benzaldehyde Derivative (I) from Benzyl Halide Derivative 3 and 2,4-dihydroxy-5-substituted Benzaldehyde 6 as Starting Materials In step (3), benzyl halide derivative 3 is reacted with 2,4-dihydroxy-5-substituted benzaldehyde 6 under a weak basic condition to selectively prepare 4-(2,3-disubstituted benzyloxy)-2-hydroxy-5-substituted benzaldehyde derivative (I).

The reaction is carried out in a conventional chemical reaction vessel, such as a flask or a reactor. Preferably, the reaction vessel is dried.

The molar ratio of the reagents benzyl halide derivative 3 and 2,4-dihydroxy-5-substituted benzaldehyde 6 in the reaction is 1:0.8-1.5; most preferably 1:1.

The preferred weak base condition in the reaction is the addition of alkali metal bicarbonate, alkali metal acetate; more preferred weak base condition is the addition of sodium hydrogen carbonate or potassium hydrogen carbonate.

The solvent used in the reaction may be selected from an aprotic polar solvent for the purpose of dissolving the reactant; the preferred aprotic solvent is selected from acetonitrile, tetrahydrofuran, diethyl ether, dioxane, dimethyl sulfoxide, N,N-dimethylformamide; the most preferred solvent is selected from acetonitrile, tetrahydrofuran, and N,N-dimethylformamide.

The reaction condition is preferably to control the reaction temperature, and the reaction temperature can be controlled between 20 and 85° C., and preferably 50-60° C. The reaction temperature varies with the solvent Beneficial Technical Effects:

The invention provides a preparation method of a compound of the formula (I), that is, 4-(2,3-disubstituted benzyloxy)-2-hydroxy-5-substituted benzaldehyde derivative, which belongs to the technical field of medicine.

The 4-(2,3-disubstituted benzyloxy)-2-hydroxy-5-substituted benzaldehyde derivative (I) is the important intermediate of immunomodulator; the preparation method has the advantages of high yield and easy industrialization; and a part of intermediates, 4-(2,3-disubstituted benzyloxy)-2-hydroxy-5-substituted benzaldehyde derivative (I), are novel compounds and potential pharmaceutical intermediates.

In the Synthetic Scheme Provided by the Present Invention:

In the step (1), the preparation method of 2-substituted-3-aryltoluene derivative 2 from 2-substituted-3-iodotoluene derivative 1 and aryl boronic acid 5 or aryl boronate as starting materials, is simple, easy to operate, mild in conditions, high in yield, and easy to industrialize; and the starting material is easily obtained. It does not require special reagents.

In the step (2), 2-substituted-3-aryltoluene derivative 2 is reacted with a brominating agent under a free radical initiating condition to prepare benzyl halide derivative 3; or 2-substituted-3-aryltoluene derivative 2 is reacted with a brominating agent under light condition to prepare benzyl halide derivative 3; wherein the reaction is mild in conditions, high in yield, easy for post-treatment and easy to industrialize, and the product is directly used for the next reaction without separation.

In the Step (3), 4-(2,3-disubstituted benzyloxy)-2-hydroxy-5-substituted benzaldehyde derivative (I) is selectively prepared from benzyl halide derivative 3 and 2,4-dihydroxy-5-substituted benzaldehyde 6 as starting materials, with the advantages of few steps, easy operation, economy, and easy industrialization.

In summary: in the synthetic scheme of the present invention, it doesn't require column chromatography separation, and doesn't require cryogenic equipment; the starting material is easily obtained, the introduction and elimination of the protecting group are not required, the reaction scheme is short, easy to operate, economical and practical, and suitable for industrial production.

The 4-(2,3-disubstituted benzyloxy)-2-hydroxy-5-substituted benzaldehyde derivative prepared by the preparation method of the invention is the important intermediate of a class of immunomodulators, Examples 2, 4, 6, 8 are an illustration of such immunomodulators. It can be seen that the compounds of Examples 2, 4, 6 and 8 can significantly inhibit the interaction between PD-1 and PD-L1, and are a novel class of immunomodulators.

Term and Abbreviation

THF: tetrahydrofuran
DMF: N,N-dimethylformamide
NBS: N-bromosuccinimide
BPO: benzoyl peroxide

DETAILED DESCRIPTION

Example 1. 4-(2-bromo-3-phenylbenzyloxy)-5-chloro-2-hydroxybenzaldehyde

2-bromo-3-phenyltoluene

To a 50 ml flask was added 2-bromo-3-iodotoluene (350 mg) and dioxane/water (volume ratio of 5/1) with stirring. The solution was bubbled with argon for 10 min to remove dissolved oxygen. Then, phenyl boronic acid (172.65 mg), cesium carbonate (961.2 mg), and triphenylphosphine palladium (40.91 mg) were sequentially added. The mixture was stirred for 12 h at 80-100° C. under argon protection. The reaction was stopped. After cooling to the room temperature, the mixture was filtered with diatomaceous earth. The filtrate was concentrated under reduced pressure and extracted with water and ethyl acetate for three times. The organic phases were combined, washed with saturated brine, and dried over anhydrous sodium sulfate. The organic layer was filtered and evaporated to dryness in vacuo, to afford 2-bromo-3-phenyltoluene as colorless oil (234 mg) in a yield of 88%. $^1$H NMR (400 MHz, DMSO-$d_6$), δ 7.49-7.29 (m, 7H, Ar—H), 7.14 (d, 1H, Ar—H), 2.42 (s, 3H, Ar—CH$_3$). MS (FAB): 248 (M+1).

2-bromo-3-phenylbenzyl Bromide 2-bromo-3-phenyltoluene (234 mg) as a starting material was taken and dissolved in 20 ml of CCl$_4$ in a 100 ml flask. To this solution was added NBS (178 mg) while stirring. And the mixture was warmed to 80° C. and refluxed. Then benzoyl peroxide (4 mg) was added, and after 2 h, benzoyl peroxide (4 mg) was added again, and the mixture was stirred for another 2 h. The reaction was stopped. After cooling to the room temperature, the mixture was quenched with water, and extracted with dichloromethane and water. The organic phase was washed with saturated brine, and dried over anhydrous sodium sulfate. The organic layer was filtered and evaporated to dryness in vacuo, to afford 2-bromo-3-phenylbenzyl bromide as yellow oil (262 mg), which was used for the next step without further purification.

4-(2-bromo-3-phenylbenzyloxy)-5-chloro-2-hydroxybenzaldehyde

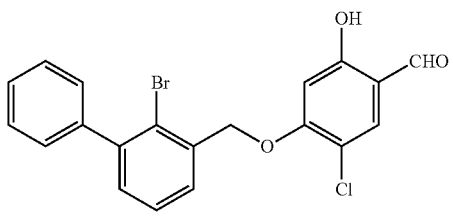 [SMILES: O=Cc1cc(Cl)c(OCc2cccc(-c3ccccc3)c2Br)cc1O]

2,4-dihydroxy-5-chlorobenzaldehyde (73.94 mg) was taken and dissolved in 6 ml of anhydrous acetonitrile in a 50 ml flask, and then sodium hydrogen carbonate (98.88 mg) was added. After stirring at the room temperature for 40 min, 2-bromo-3-phenylbenzyl bromide (192 mg, dissolved in 8 ml of DMF) was slowly added to the reaction mixture via a constant pressure dropping funnel, and heated to reflux until the reaction was completed. After cooling to the room temperature, the mixture was extracted with water and ethyl acetate. The organic phase was washed with saturated brine, and dried over anhydrous sodium sulfate, then filtrated and evaporated to dryness in vacuo, to afford 4-(2-bromo-3-phenylbenzyloxy)-5-chloro-2-hydroxybenzaldehyde as a white solid (192 mg) in a yield of 85%. $^1$H NMR (400 MHz, DMSO-$d_6$) δ 10.99 (s, 1H, —OH), 10.03 (s, 1H, —CHO), 7.64 (d, 1H, Ar—H), 7.57 (d, 1H, Ar—H), 7.45 (m, 4H, Ar—H), 7.37 (d, 2H, Ar—H), 6.67 (d, 1H, Ar—H), 6.59 (s, 1H, Ar—H), 5.25 (s, 2H, —CH$_2$—). MS (FAB): 418(M+1).

Example 2

N-acetylaminoethyl-4-(2-bromo-3-phenylbenzyloxy)-2-(3-cyanobenzyloxy)-5-chlorobenzylamine

4-(2-bromo-3-phenylbenzyloxy)-5-chloro-2-(3-cyanobenzyloxy) benzaldehyde 4-(2-bromo-3-phenylbenzyloxy)-2-hydroxy-5-chlorobenzaldehyde (100 mg) was dissolved in 6 ml of DMF in a 50 ml flask, and then cesium carbonate (127.53 mg) was added. After stirring at the room temperature for 15 min, a solution of m-cyanobenzyl bromide (76.65 mg) in DMF (4 ml) was added dropwise. After the mixture was stirred at 80° C. for 2 h, the reaction was stopped. After cooling to the room temperature, the mixture was extracted with water and ethyl acetate. The organic phase was washed with saturated brine, and dried over anhydrous sodium sulfate, then filtrated and evaporated to dryness in vacuo. The crude residue was purified by silica gel column chromatography to afford a white solid (103 mg). $^1$H NMR (400 MHz, DMSO-$d_6$) δ 10.26 (s, 1H, —CHO), 8.00 (s, 1H, Ar—H), 7.83 (dd, 2H, Ar—H), 7.72 (d, 1H, Ar—H), 7.61 (t, 2H, Ar—H), 7.55-7.23 (m, 7H, Ar—H), 6.95 (s, 1H, Ar—H), 6.81 (d, 1H, Ar—H), 5.35 (s, 2H, —CH$_2$—), 5.30 (s, 2H, —CH$_2$—). MS (FAB): 509(M+1).

N-Acetylaminoethyl-4-(2-bromo-3-phenylbenzyloxy)-2-(3-cyanobenzyloxy)-5-chlorobenzyl Amine

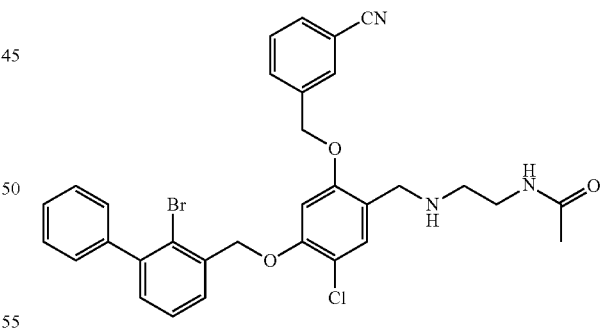

4-(2-bromo-3-phenylbenzyloxy)-2-(3-cyanobenzyloxy)-5-chlorobenzaldehyde (50.8 mg) was dissolved in 5 ml of DMF, and then 2-acetamidoethylamine (31.25 mg) and acetic acid glacial (36.75 mg) were added. After stirring at the room temperature for 20 min, sodium cyanoborohydride (19.23 mg) was added and the mixture was stirred at 25° C. for 14 h. The reaction was stopped. The mixture was extracted with water and ethyl acetate. The organic phase was washed with saturated brine, and dried over anhydrous sodium sulfate, then filtrated and evaporated to dryness in vacuo. The residue was purified by silica gel column chromatography to afford a white solid (55 mg). $^1$H NMR (500 MHz, DMSO-$d_6$) δ 8.00 (s, 1H, —ArH), 7.86 (dd, 2H, —ArH), 7.69-7.62 (m, 2H, —ArH), 7.53 (d, 2H, —ArH), 7.50 (d, 2H, —ArH), 7.46 (d, 1H, —ArH), 7.41 (t, 3H, —ArH), 7.07 (s, 1H, —ArH), 5.33 (s, 2H, —CH$_2$—), 5.32 (s, 2H, —CH$_2$—), 3.89 (s, 2H, —CH$_2$—), 3.25 (m, 2H, —CH$_2$—), 2.74 (t, 2H, —CH$_2$—), 1.83 (s, 3H, —COCH$_3$). MS (FAB): 620(M+1).

Example 3

4-(2-bromo-3-(2,3-dihydrobenzo[b][1,4]dioxin-6-yl)benzyloxy)-5-chloro-2-hydroxybenzaldehyde 2-bromo-3-(2,3-dihydrobenzo[b][1,4]dioxin-6-yl)toluene The procedure was the same as in Example 1, except that 2-(2,3-dihydrobenzo[b][1,4]dioxin-6-yl)-4,4,5,5-tetramethyl-1,3,2-dioxaborolane was used in place of phenyl boronic acid, [1,1'-bis (diphenylphosphino)ferrocene]dichloropalladium was used in place of triphenylphosphine palladium, potassium carbonate was used in place of cesium carbonate to afford 2-bromo-3-(2,3-dihydrobenzo[b][1,4]dioxin-6-yl) toluene as pale yellow oil. $^1$H NMR (400 MHz, Chloroform-d) δ 7.21 (d, 2H, —ArH), 7.11 (m, 1H, —ArH), 6.90 (d, 2H, —ArH), 6.86 (d, 1H, —ArH), 4.30 (m, 4H, —OCH$_2$CH$_2$O—), 2.48 (s, 3H, —CH$_3$).

4-(2-bromo-3-(2,3-dihydrobenzo[b][1,4]dioxin-6-yl)benzyloxy)-2-hydroxy-5-chlorobenzaldehyde

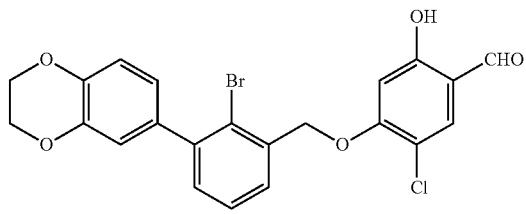 [SMILES: O=Cc1cc(Cl)c(OCc2cccc(-c3ccc4c(c3)OCCO4)c2Br)cc1O]

The procedure was the same as in Example 1, except that 2-bromo-3-(2,3-dihydrobenzo[b][1,4]dioxin-6-yl) toluene was used in place of 2-Bromo-3-methyl-1,1'-biphenyl to effect bromination; the bromide, without further purification, was reacted directly with 2,4-dihydroxy-5-chlorobenzaldehyde to afford a white solid. $^1$H NMR (400 MHz, DMSO-$d_6$) δ 10.91 (s, 1H, —OH), 9.95 (s, 1H, —CHO), 7.57 (d, 1H, —ArH), 7.45 (d, 1H, —ArH), 7.37 (t, 1H, —ArH), 7.25 (d, 1H, —ArH), 6.84 (d, 1H, —ArH), 6.78 (s, 1H, —ArH), 6.74 (d, 1H, —ArH), 6.59 (d, 1H, —ArH), 6.51 (s, 1H, —ArH), 5.16 (s, 2H, —CH$_2$—), 4.20 (m, 4H, —OCH$_2$CH$_2$O—). MS (FAB): 476(M+1).

Example 4

N-(Hydroxyethyl)-4-(2-bromo-3-(2,3-dihydrobenzo[b][1,4]dioxin-6-yl)benzyloxy)-5-Chloro-2-(3-cyanobenzyloxy)benzylamine 4-(2-bromo-3-(2,3-dihydrobenzo[b][1,4]dioxin-6-yl)benzyloxy)-5-chloro-2-(3-cyanobenzyloxy) benzaldehyde The procedure was the same as in Example 2, except that 4-(2-bromo-3-(2,3-dihydrobenzo[b][1,4]dioxin-6-yl)benzyloxy)-2-hydroxy-5-Chlorobenzaldehyde was used in place of 4-(2-bromo-3-phenylbenzyloxy)-2-hydroxybenzaldehyde to afford a white solid. $^1$H NMR (400 MHz, DMSO-$d_6$) δ 10.28 (s, 1H, —CHO), 8.01 (s, 1H, —ArH), 7.85 (dd, 2H, —ArH), 7.74 (d, 1H, —ArH), 7.63 (t, 1H, —ArH), 7.58 (d, 1H, —ArH), 7.46 (t, 1H, —ArH), 7.35 (d, 1H, —ArH), 6.94 (d, 2H, —ArH), 6.87 (s, 1H, —ArH), 6.82 (d, 2H, —ArH), 5.36 (s, 2H, —CH$_2$—), 5.30 (s, 2H, —CH$_2$—), 4.29 (m, 4H, —OCH$_2$CH$_2$O—). MS (FAB): 567(M+1).

N-(Hydroxyethyl)-4-(2-bromo-3-(2,3-dihydrobenzo[b][1,4]dioxin-6-yl)benzyloxy)-5-Chloro-2-(3-cyanobenzyloxy)benzylamine

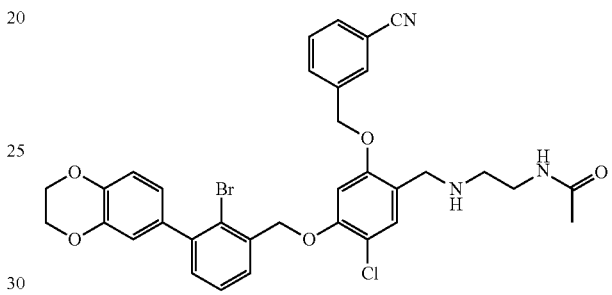

The procedure was the same as in Example 2, except that 4-(2-bromo-3-(2,3-dihydrobenzo[b][1,4]dioxin-6-yl)benzyloxy)-2-(3-cyanobenzyloxy) benzaldehyde was used in place of 4-(2-bromo-3-phenylbenzyloxy)-2-(3-cyanobenzyloxy)-5-Chlorobenzaldehyde to afford an off-white solid powder. $^1$H NMR (400 MHz, DMSO-$d_6$) δ 8.74 (s, 1H, —NH—), 8.14 (m, 1H, —CONH—), 8.00 (s, 1H, —ArH), 7.85 (dd, 2H, —ArH), 7.63 (t, 1H, —ArH), 7.54 (d, 1H, —ArH), 7.50-7.37 (m, 2H, —ArH), 7.33 (d, 1H, —ArH), 6.94 (d, 1H, —ArH), 6.86 (s, 2H, —ArH), 6.82 (d, 1H, —ArH), 6.74 (d, 1H, —ArH), 5.27 (s, 2H, —CH$_2$—), 5.20 (s, 2H, —CH$_2$—), 4.29 (m, 4H, —OCH$_2$CH$_2$O—), 4.13 (s, 2H, —CH$_2$—), 3.34-3.39 (m, 2H, —CH$_2$—), 2.96 (m, 2H, —CH$_2$—), 1.82 (s, 3H, —COCH$_3$). MS (FAB): 678 (M+1).

Example 5

4-(2-methyl-3-(2,3-dihydrobenzo[b][1,4]dioxin-6-yl)benzyloxy)-5-chloro-2-hydroxybenzaldehyde

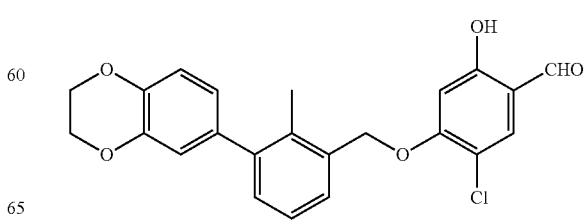

The procedure was the same as in Example 1, except that 2-methyl-3-iodotoluene was used in place of 2-bromo-3-iodotoluene as the starting material, to afford 4-(2-methyl-3-(2,3-dihydrobenzo[b][1,4]dioxin-6-yl)benzyloxy)-5-chloro-2-hydroxybenzaldehyde as a white solid. The yield in the last step was 78%. MS (FAB): 411 (M+1).

Example 6

(R)—N-[2-(5-cyanopyridine-3-methyleneoxy)-4-(2-methyl-3-(2,3-dihydrobenzo[b][1,4]dioxin-6-yl)benzyloxy)-5-chlorobenzyl]-3-(pyridin-3-yl)alanine

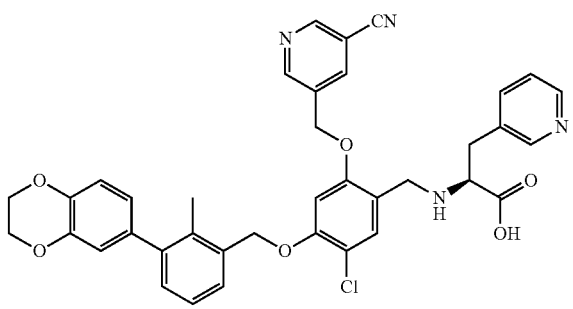 [SMILES: Cc1c(COc2cc(OCc3cncc(C#N)c3)c(CN[C@@H](Cc3cccnc3)C(=O)O)cc2Cl)cccc1-c1ccc2c(c1)OCCO2]

The procedure was the same as in Example 2, except that 5-cyanopyridine-3-methylene bromide was used in place of m-cyanobenzyl bromide, and asparaginate was used in place of 2-acetylaminoethylamine, to afford (R)—N-[2-(5-cyanopyridine-3-methyleneoxy)-4-(2-methyl-3-(2,3-dihydrobenzo[b][1,4]dioxin-6-yl)benzyloxy)-5-chlorobenzyl]-3-(pyridin-3-yl) alanine as a white solid in a yield of 48%. MS (FAB): 678 (M+1)

Example 7

5-bromo-4-(2-cyano-3-(2,3-dihydrobenzo[b][1,4]dioxin-6-yl)benzyloxy)-2-hydroxybenzaldehyde

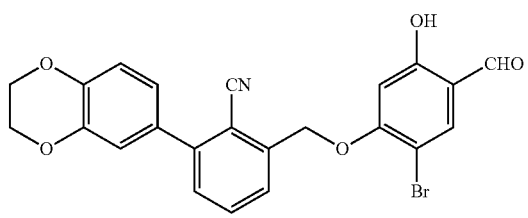 [SMILES: N#Cc1c(COc2cc(O)c(C=O)cc2Br)cccc1-c1ccc2c(c1)OCCO2]

The procedure was the same as in Example 1, except that 2-cyano-3-iodotoluene was used in place of 2-bromo-3-iodotoluene, and 2, 4-dihydroxy-5-bromobenzaldehyde was used in place of 2, 4-dihydroxy-5-chlorobenzaldehyde, to afford 5-bromo-4-(2-cyano-3-(2,3-dihydrobenzo[b][1,4]dioxin-6-yl) benzyloxy)-2-hydroxybenzaldehyde as a white solid. The yield in the last step was 76%. MS (FAB): 467 (M+1).

Example 8

N-(2-acetylaminoethyl)-2-(3-cyanobenzyloxy)-4-(2-cyano-3-(2,3-dihydrobenzo[b][1,4]dioxin-6-yl)benzyloxy)benzylamine

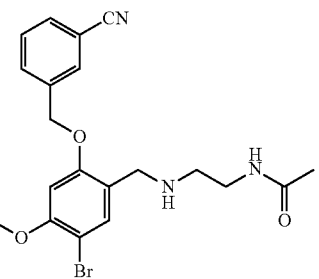

The procedure was the same as in Example 2, except that 5-bromo-4-(2-cyano-3-(2,3-dihydrobenzo[b][1,4]dioxin-6-yl) benzyloxy)-2-hydroxybenzaldehyde as the starting material, to afford N-(2-Acetylaminoethyl)-2-(3-cyanobenzyloxy)-4-(2-cyano-3-(2,3-dihydrobenzo[b][1,4]dioxin-6-yl) benzyloxy) benzylamine as a white solid in a yield of 46%. MS (FAB): 668 (M+1).

Note: Examples 1, 3, 5, and 7 are intermediate 2-hydroxy-4-(2,3-disubstituted benzyloxy)-5-substituted benzaldehyde derivative (I).

Examples 2, 4, 6, and 8 are immunomodulatory compounds prepared on the basis of Examples 1, 3, 5, and 7, respectively.

The compounds of Examples 5, 6, 7, and 8 are known compounds.

Pharmacological Experiments

In vitro activity evaluation: Cisbio HTRF binding assay kit was applied for the detection method of in vitro enzymology level.

Screening Principles and Methods of PD-1/PD-L1 Small Molecule Inhibitors

1) Principle: PD-1 protein is with HIS tag, and PD-1 ligand PD-L1 is with hFc tag. Eu labeled anti-hFc antibody and XL665 labeled anti-HIS antibody are combined with the above two label proteins respectively. After laser excitation, energy can be transferred from donor Eu to receptor XL665, allowing XL665 to glow. After adding inhibitors (compounds or antibodies), blocking the binding of PD-1 and PD-L1 makes the distance between Eu and XL665 far away, the energy can not be transferred, and XL665 does not glow.

2) Experimental method: Reagents should be dispensed in the following order. For 384-well white ELISA plate, 2 μl of diluent or target compound diluted with diluent was added to each well, and then 4 μl of PD-1 protein and 4 μl of PD-L1 protein were added per well, incubated for 15 min at the room temperature; and 10 μl of anti-Tag1-Eu3$^+$ and anti-Tag2-XL665 was added per well and incubated for 1 h at the room temperature and the fluorescence signals at 665 nm and 620 nm were measured. HTRF rate=(665 nm/620 nm)*$10^4$. 8-10 concentrations were detected for each compound and $IC_{50}$ was calculated by Graphpad software.

3. Screening results:

| Example | IC$_{50}$ (M) | Example | IC$_{50}$ (M) |
|---------|---------------|---------|---------------|
| 2 | 6.23 × 10$^{-8}$ | 4 | 2.68 × 10$^{-7}$ |
| 6 | 3.5 × 10$^{-8}$ | 8 | 7.12 × 10$^{-9}$ |

What is claimed is:

1. A method for preparing 4-(2, 3-disubstituted benzyloxy)-2-hydroxy-5-substituted benzaldehyde derivative (I):

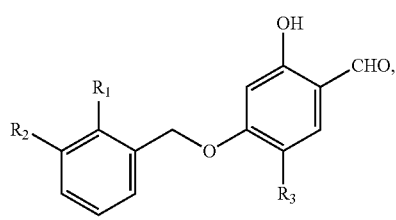

wherein the method comprises the following steps:
1) preparing 3-aryl-2-substituted toluene derivative 2 from 3-iodo-2-substituted toluene derivative 1 and aryl boronic acid 5, or an aryl boronate thereof, as starting materials:

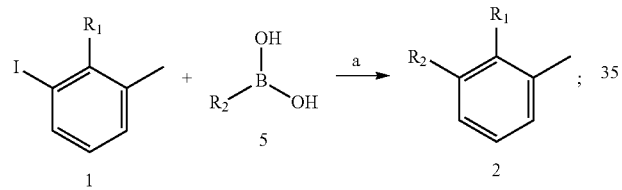

wherein "a" means that 3-iodo-2-substituted toluene derivative 1 and aryl boronic acid 5, or an aryl boronate thereof, are subjected to a Suzuki-Miyaura coupling reaction to form 3-aryl-2-substituted toluene derivative 2 in the presence of a palladium catalyst and a base;

2) preparing benzyl halide derivative 3 from 3-aryl-2-substituted toluene derivative 2 as a starting material:

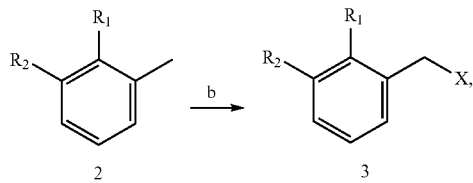

wherein "b" means that 3-aryl-2-substituted toluene derivative 2 is reacted with a halogenating agent under radical-initiating condition to prepare a benzyl halide derivative 3;

3) preparing 4-(2, 3-disubstituted benzyloxy)-2-hydroxy-5-substituted benzaldehyde derivative (I) from benzyl halide derivative 3 and 2,4-dihydroxy-5-substituted benzaldehyde 6 as starting materials:

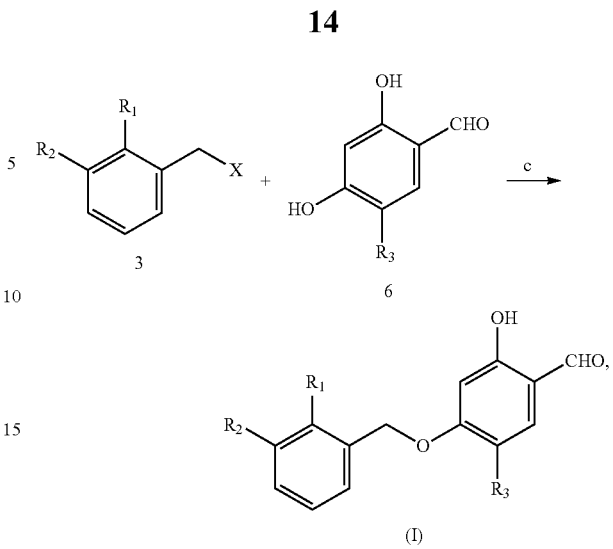

wherein "c" means that benzyl halide derivative 3 is reacted with 2, 4-dihydroxy-5-substituted benzaldehyde 6 in a weak basic condition to selectively prepare a 4-(2, 3-disubstituted benzyloxy)-2-hydroxy-5-substituted benzaldehyde derivative (I);

wherein:
R$_1$ is selected from fluorine, chlorine, bromine, methyl, and cyano;
R$_2$ is selected from

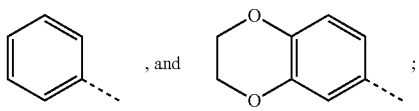

R$_3$ is selected from hydrogen, methyl, ethyl, fluorine, chlorine, and bromine;
X selected from bromine, chlorine, and iodine.

2. The method according to claim 1, wherein the palladium catalyst is selected from zero-valent palladium and divalent palladium compounds.

3. The method according to claim 2, wherein the zero-valent palladium catalyst is selected from triphenylphosphine palladium and tetrakis(triphenylphosphine)palladium, and the divalent palladium catalyst is PdCl$_2$ (dppf).

4. The method according to claim 1, wherein the base is selected from alkali metal carbonate and alkali metal acetate.

5. The method according to claim 4, wherein the alkali metal carbonate is selected from cesium carbonate, potassium carbonate, and sodium carbonate, and the alkali metal acetate is selected from sodium acetate and potassium acetate.

6. The method according to claim 1, wherein the halogenating agent is selected from N-bromosuccinimide, N-chlorosuccinimide, phenyltrimethylammonium tribromide, and elemental bromine.

7. The method according to claim 1, wherein the radical initiating condition is the addition of a radical initiator, or light, or a combination thereof.

8. The method according to claim 7, wherein the radical initiator is selected from benzoyl peroxide and m-chloroperoxybenzoic acid.

9. The method according to claim 1, wherein the weak base condition is the addition of an alkali metal hydrogen carbonate or an alkali metal acetate.

10. The method according to claim 9, wherein the alkali metal hydrogen carbonate is selected from sodium hydrogen carbonate and potassium hydrogen carbonate.

* * * * *

UNITED STATES PATENT AND TRADEMARK OFFICE
CERTIFICATE OF CORRECTION

PATENT NO. : 10,815,208 B2
APPLICATION NO. : 16/303650
DATED : October 27, 2020
INVENTOR(S) : Zhiqiang Feng et al.

Page 1 of 1

It is certified that error appears in the above-identified patent and that said Letters Patent is hereby corrected as shown below:

On the Title Page

Item (30), the following Foreign Application Priority Data:
"May 23, 2016  (CN) ...................... 2016 1 0343960"
Should read:
--May 23, 2016 (CN) ...................... 201610343960.7--

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*